United States Patent
Kelley (10) Patent No.: US 9,668,760 B2
(45) Date of Patent: Jun. 6, 2017

(54) METHODS AND SYSTEMS FOR PREPARING THE ACETABULUM TO RECEIVE AN ACETABULAR COMPONENT IN A HIP REPLACEMENT SURGICAL PROCEDURE

(71) Applicant: Scott Kelley, Chapel Hill, NC (US)

(72) Inventor: Scott Kelley, Chapel Hill, NC (US)

( * ) Notice: Subject to any disclaimer, the term of this patent is extended or adjusted under 35 U.S.C. 154(b) by 327 days.

(21) Appl. No.: 14/453,358

(22) Filed: Aug. 6, 2014

(65) Prior Publication Data
US 2015/0045802 A1 Feb. 12, 2015

Related U.S. Application Data

(60) Provisional application No. 61/863,641, filed on Aug. 8, 2013.

(51) Int. Cl.
*A61B 17/16* (2006.01)
*A61B 17/17* (2006.01)
*A61F 2/34* (2006.01)
*A61B 90/00* (2016.01)

(52) U.S. Cl.
CPC ...... *A61B 17/1746* (2013.01); *A61B 17/1664* (2013.01); *A61B 2090/034* (2016.02); *A61F 2/34* (2013.01)

(58) Field of Classification Search
CPC .......... A61B 17/1746; A61B 17/1664
See application file for complete search history.

(56) References Cited

U.S. PATENT DOCUMENTS

| 4,528,980 | A | * | 7/1985 | Kenna | A61B 17/1746 606/102 |
| 5,919,195 | A | * | 7/1999 | Wilson | A61B 17/1666 606/80 |
| 6,395,005 | B1 | * | 5/2002 | Lovell | A61B 17/1666 606/91 |
| 6,743,235 | B2 | | 6/2004 | Subba Rao | |
| 7,004,972 | B2 | | 2/2006 | Yoon | |
| 8,267,938 | B2 | | 9/2012 | Murphy | |
| 8,900,244 | B2 | * | 12/2014 | Meridew | A61F 2/4609 606/91 |
| 8,961,521 | B2 | * | 2/2015 | Keefer | A61B 17/1659 606/171 |

(Continued)

OTHER PUBLICATIONS

Callaghan et al., ed. The Adult Hip. vol. 2, 2nd ed. Chapter 60, pp. 884-910, and Chapter 70, pp. 1025-1035. 2007. Lippincott Williams & Wilkins, Philadephia, Pa.

(Continued)

*Primary Examiner* — David Bates
(74) *Attorney, Agent, or Firm* — Coats & Bennett, PLLC (57) ABSTRACT

Methods and devices for preparing an acetabulum for receiving an acetabular component in a hip replacement procedure. The methods may include aligning a first guide in an acetabular notch of the acetabulum and determining a reference point in the acetabulum. The first guide is removed from the acetabulum and then a second guide is positioned in the acetabulum and oriented with the reference point. While the second guide is positioned in the acetabulum, the acetabular margin is reamed with a reamer. During reaming, the reamer is contacted against a rim of the second guide which prevents additional reaming of the acetabular notch below the rim of the second guide.

17 Claims, 10 Drawing Sheets

(56) References Cited

U.S. PATENT DOCUMENTS

| | | | |
|---|---|---|---|
| 9,011,456 B2* | 4/2015 | Ranawat | A61F 2/4609 606/91 |
| 9,186,158 B2* | 11/2015 | Anthony | A61B 17/1659 |
| 9,339,278 B2* | 5/2016 | Meridew | A61B 17/1659 |
| 2004/0236341 A1 | 11/2004 | Petersen | |
| 2008/0009874 A1* | 1/2008 | Meridew | A61B 17/1666 606/81 |
| 2011/0046745 A1 | 2/2011 | Daniels et al. | |
| 2011/0112540 A1 | 5/2011 | McLean et al. | |
| 2011/0208318 A1 | 8/2011 | Sudmann | |
| 2012/0041445 A1* | 2/2012 | Roose | A61B 17/1746 606/96 |
| 2012/0184964 A1 | 7/2012 | Hudak, Jr. et al. | |
| 2012/0245647 A1 | 9/2012 | Kunz et al. | |
| 2012/0265208 A1* | 10/2012 | Smith | A61B 17/1626 606/87 |
| 2013/0006255 A1 | 1/2013 | Murphy | |
| 2013/0245631 A1* | 9/2013 | Bettenga | A61B 17/1666 606/91 |
| 2014/0163564 A1 | 6/2014 | Bollinger | |
| 2014/0180296 A1* | 6/2014 | Gillman | A61F 2/30942 606/87 |

OTHER PUBLICATIONS

Hansen et al. "The Rottinger approach for total hip arthroplasty: technique and review of the literature" Curr Rev. Musculoskelet Med (2011) 4:132-138. Springer, Berlin, Germany.

"Zimmer Natural-Hip™ System Surgical Technique" Informational Booklet. 25 pages. 2005. Zimmer, Inc. Warsaw, IN.

"CPT® 12/14 Hip System. Surgical Technique for Primary Hip Arthroplasty" Informational Booklet. 27 pages. 2002. Zimmer, Inc. Warsaw, IN.

"Alloclassic® Hip System Surgical Technique" Informational Booklet. 20 pages. 2003. Zimmer, Inc. Warsaw, IN.

"ZMR® Hip System" Informational literature, 20 pages. 2003. Zimmer, Inc. Warsaw, IN.

"Zimmer® M/L Taper Hip Prosthesis. Surgical Technique" Informational Booklet. 16 pages. 2010. Zimmer, Inc. Warsaw, IN.

"Synergy Cemented Stem Surgical Technique" Informational Booklet, 31 pages. 2004. Smith & Nephew, Inc., Memphis, TN.

"Synergy Cementless Stem Surgical Technique" Informational Booklet, 32 pages. 2004. Smith & Nephew, Inc., Memphis, TN.

"ZMR Revision Taper Hip Prosthesis, Surgical Technique for Revision Hip Arthroplasty" 26 pages. 1999. Zimmer, Inc. Warsaw, IN.

"Summit® titanium tapered stem." Product description and illustration,1 page. 2001. DePuy Orthopaedics, Inc., Warsaw, IN.

Morrey, Bernard, ed. Joint Replacement Arthroplasty. Chapter 44, pp. 619-638. 1991. Churchill Livingstone, Inc., New York, NY.

Biomet. "Signature Hip Technology Personalized Patient Care." Product information, 8 pages. 2013. Biomet, Inc. Warsaw, IN.

Mohammed, A., et al., "Removal of well-fixed hip resurfacing acetabular components: A technical note." Orthopedics Today, Jun. 2009. Accessed at http://www.healio.com/orthopedics/hip/news/print/orthopedics-today/%7Be8e2cd81-f673-4bc9-8809-24938d3d74da%7D/removal-of-well-fixed-hip-resurfacing-acetabular-components-a-technical-note.

Zimmer. "Explant Acetabular Cup Removal System Surgical Technique." Product Overview. 10 pages. 2011. Zimmer, Inc., Warsaw, IN.

Digioia, A.M., et al., "HipNav: Pre-operative Planning and Intraoperative Navigational Guidance for Acetabular Implant Placement in Total Hip Replacement Surgery." Proc. of the Computer Assisted Orthopaedic Surgery Symposium, Bern, Switzerland, Nov. 1995.

"DePuy Revision Solutions. Hip Extraction Instrumentation Product Overview." 16 pages. 2009. DePuy Orthopaedics, Inc. Warsaw, IN.

"Moreland Cementless Hip Revision Instrumentation." Product Overview. 12 pages. 1998. DePuy Orthopaedics, Inc. Warsaw, IN.

"Hip Labral Disorders." Conolty, Karolyn, ed., et al. Physiopedia. Accessed Aug. 28, 2014, at http://www.physio-pedia.com/Hip_Labral_Tears.

Buller, L., et al., "The Use of Patient-Specific Instrumentation Improves the Accuracy of Acetabular Component Placement." The Journal of Arthroplasty 28(4): 631-636. Apr. 2013. Elsevier, Amsterdam, NL.

Sotereanos, N.G., et al., "Using Intraoperative Pelvic Landmarks for Acetabular Component Placement in Total Hip Arthroplasty." The Journal of Arthroplasty 21(6): 832-840. Sep. 2006. Elsevier, Amsterdam, NL.

Zimmer. "Trabecular Metal Modular Acetabular System Surgical Technique." 15 pages. 2011 Zimmer, Inc., Warsaw, IN.

Reamer. Smith & Nephew Catalog. Viewed online Jul. 25, 2013 at http://orthocatalog.smithnephew.com/?cat=3&cat1=5&cat2=17&cat3=56&pID=1782. Smith & Nephew, Inc., London, UK.

"Direct Manufacture of Medical Implants Set to Grow." Accessed online Jul. 25, 2013, at http://www.rapidtoday.com/implant.html. Rapid Publishing, LLC.

* cited by examiner

METHODS AND SYSTEMS FOR PREPARING THE ACETABULUM TO RECEIVE AN ACETABULAR COMPONENT IN A HIP REPLACEMENT SURGICAL PROCEDURE

CROSS-REFERENCE TO RELATED APPLICATIONS

The present application claims the benefit of U.S. Application No. 61/863,641 filed on Aug. 8, 2013, and entitled Methods and Systems for Preparing the Acetabulum to Receive an Acetabular Component in a Hip Replacement Surgical Procedure. This application is hereby incorporated by reference in its entirety.

BACKGROUND

Hip replacement procedures involve the replacement of the hip joint formed by the head of the femur and the acetabulum of the pelvic bone. Hip replacement procedures include the preparation of the femur for receipt of a femoral component and preparation of the acetabulum to receive an acetabulum component. The two components engage together to replace the hip joint. Numerous surgical approaches exist for performing the hip replacement procedure.

The placement of the acetabulum component in the acetabulum is critical to the success of the hip replacement procedure. Therefore, the method of determining the position of the acetabular component and preparation of the acetabulum are key features. Prior art methods have used a variety of different methods of determining the position of the acetabular component. Many methods utilize the acetabular margin as a baseline for determining the positioning of the acetabular component. However, there is a wide variation in the bony geometry of these features between different patients. Therefore, these methods result in different placements of the various guides and component between the different patients.

Other methods require complicated devices and/or methods that are often difficult for a surgeon to use and perform. These devices and methods require a large amount of initial training by the surgeon prior to use during a surgical procedure. Further, the devices and methods are often not favored by surgeons due to their complexity and difficulty in use.

SUMMARY

The present application is methods and devices for preparing an acetabulum to receive an acetabular component. The methods involve remaining the peripheral rim of the acetabulum in relationship to the teardrop. This rim can capture Saturn ring modifications to other acetabular instrumentation.

One embodiment is directed to a method of preparing an acetabulum for receiving an acetabular implant during a hip replacement procedure. The method includes: aligning a first guide in an acetabular notch of the acetabulum and determining a reference point in the acetabulum; removing the first guide from the acetabulum; after removing the first guide, positioning a second guide in the acetabulum and orienting the second guide with the reference point; while the second guide is positioned in the acetabulum, reaming an acetabular margin of the acetabulum with a reamer; and contacting the reamer against a rim of the second guide and preventing additional reaming of the acetabular notch below the rim of the second guide.

Aligning the first guide in the acetabular notch of the acetabulum and determining the reference point in the acetabulum may include positioning a concave body of the first guide in the acetabulum and an extension that extends from the body in the acetabular notch.

The second guide may include a partial spherical shape with a closed end that faces in towards the acetabulum and an open end that forms the rim and faces outward away from the acetabulum.

The method may also include attaching an alignment member to the acetabulum at the reference point and positioning the second guide in the acetabulum while the alignment member is attached to the acetabulum. This may also include reaming the acetabular margin while the alignment member is attached to the acetabulum.

The method may also include positioning an opening of the first guide in the acetabulum and determining the reference point in the acetabulum.

The method may also include positioning a first portion of the first guide in the acetabulum and positioning a second portion of the first guide in the acetabular notch.

Another embodiment is directed to a method of preparing an acetabulum for receiving an acetabular implant during a hip replacement procedure. The method includes: aligning a guide in the acetabulum by simultaneously positioning a body of the guide in the acetabulum and an extension that extends from the body in an acetabular notch with the body of the guide including a concave shape that matches the acetabulum; determining an alignment point in the acetabulum; attaching an alignment member to the acetabulum at the alignment point; inserting a partially spherical cutting guide over the alignment member and aligning the cutting guide in the acetabulum with a flat rim at an open side of the cutting guide positioned at an acetabular margin of the acetabulum; and reaming the acetabular margin while the cutting guide is positioned in the acetabulum and controlling a depth of the reaming with the flat rim of the cutting guide.

Determining the alignment point in the acetabulum using the guide may include aligning an opening in the guide with a center of the acetabulum by positioning the extension of the guide in the acetabular notch.

Attaching the alignment member to the acetabulum at the alignment point may include inserting the alignment member through the body of the guide and attaching the alignment member to the acetabulum.

The method may also include removing the guide from the acetabulum prior to attaching the alignment member to the acetabulum.

The method may include aligning the guide in the acetabulum and positioning the body of the guide in the acetabular margin.

Reaming of the acetabular margin may include inserting a reamer over the alignment member and reaming the acetabular margin.

The method may also include positioning a tube that extends outward from an inner side of the body of the guide at a center of the acetabulum.

Another embodiment is directed to a method of preparing an acetabulum for receiving an acetabular implant during a hip replacement procedure. The method includes: positioning a portion of a guide in an acetabular notch of the acetabulum and simultaneously positioning a second portion of the guide in the acetabulum; using the second portion of the guide and determining a reference point in the acetabulum with the reference point being positioned in the acetabular margin; attaching an attachment member to the acetabulum at the reference point with a free end of the attachment member extending outward from a surface of the acetabulum; attaching a cutting guide to the attachment member and aligning the cutting guide in the acetabulum with a flat rim at an open side of the cutting guide positioned at an acetabular margin of the acetabulum; and reaming the acetabular margin while the cutting guide is positioned in the acetabulum and controlling a depth of the reaming with the flat rim of the cutting guide.

The method may also include removing the guide from the acetabulum prior to attaching the cutting guide with the attachment member.

Using the second portion of the guide and determining the reference point in the acetabulum may include aligning an opening in the second portion of the guide with a center of the acetabulum.

The method may also include reaming the acetabular margin while the attachment member is attached to the acetabulum.

One embodiment is directed to a method of preparing an acetabulum that includes accessing an acetabular notch of the acetabulum. The method includes orienting one or more cutting tools in the acetabulum relative to the acetabular notch and preparing the acetabulum.

Another method is directed to preparing an acetabulum that includes aligning a drill guide in an acetabular notch and determining a point in the acetabulum. The method includes positioning a cutting guide relative to the point. The method includes preparing an acetabular margin of the acetabulum relative to the cutting guide. The method also includes reaming the acetabulum with the reamed acetabular margin acting as a depth guide.

The method may also include creating the drill guide based on imaging of the bony geometry of the acetabulum.

The method may also include creating the drill guide intra-operatively.

The method may also include mounting an alignment pin in the acetabulum at the point.

These various aspects may be used together in a single procedure. Alternatively, the various aspects may be used separately.

DETAILED DESCRIPTION

The present application is directed to systems and methods for preparing the acetabulum for receiving an acetabular component as part of a hip replacement surgical procedure. The methods and devices key the positioning within the acetabulum on the acetabular notch. This bony feature is consistent between patients with varying acetabulum bony anatomical features.

Figure 1:
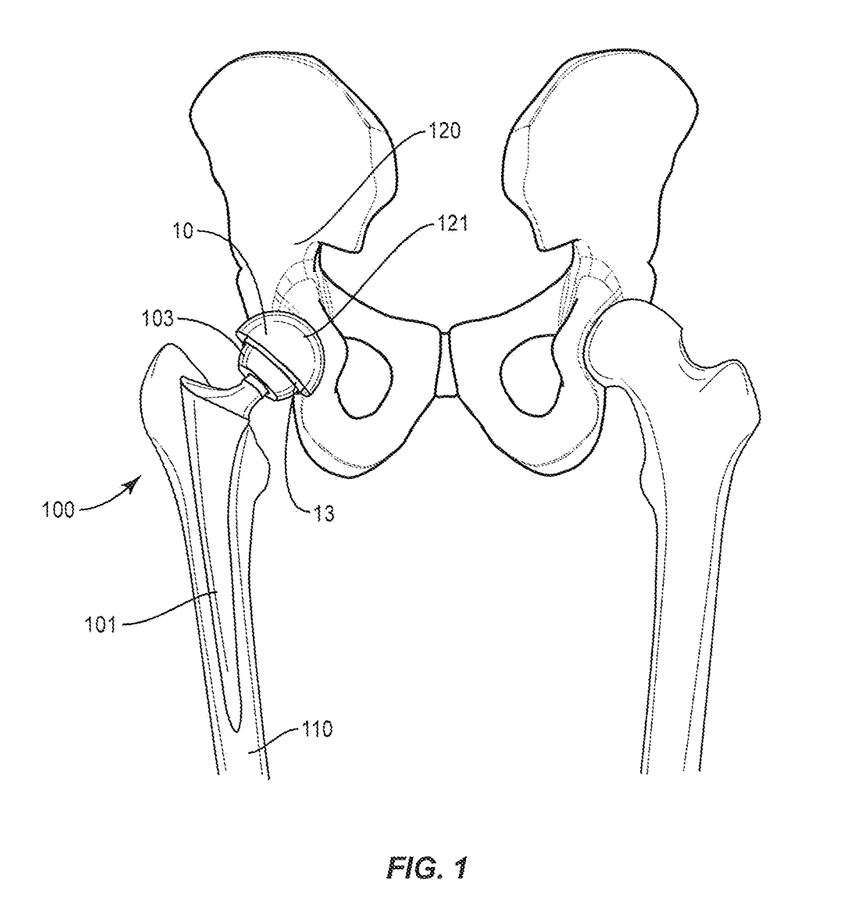
FIG. 1 is a schematic view of a hip replacement implant including a femoral component and an acetabular component implanted within a patient.

FIG. 1 illustrates a hip replacement implant 100 positioned within a patient. The implant 100 includes a femoral component 101 that is attached to the femur 110, and an acetabular component 10 that is attached to the acetabulum 121 in the pelvis 120. The femoral component 101 includes a head 103 that seats within a receptacle 13 of the acetabular component 10. This replacement joint replicates the hip joint and provides for pivoting movement of the femur 110 relative to the pelvis 120.

Figure 2:
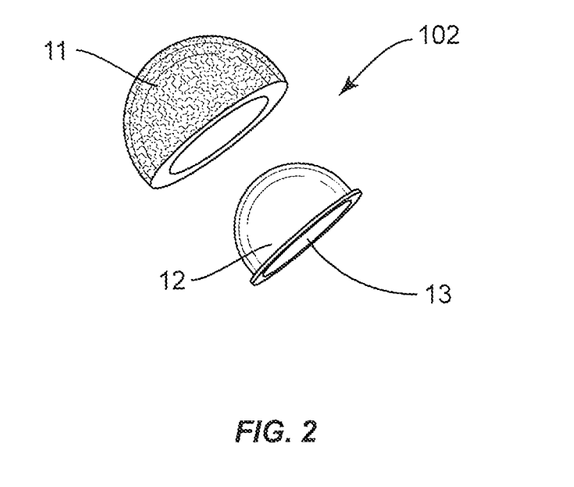
FIG. 2 is a perspective view of an acetabular component for implanting with an acetabulum.

The acetabular component 10 is configured to attach to the acetabulum 121 and receive the head 103 of the femoral component 101. The acetabular component 10 general includes a concave body with a first open side having the receptacle 13 that receives the head 103, and an opposing closed side configured to seat with the acetabulum 121. FIG. 2 illustrates one embodiment of the acetabular component 10 that includes a shell 11 and a liner 12 that each includes a concave shape. The shell 11 is initially attached to the acetabulum 121 with the liner 12 fitting within the shell 11. The liner 12 includes the receptacle 13 to engage with the head 103 of the femoral component 101 to form the hip joint.

Examples of implants 100 include but are not limited to a Synergy hip system available from Smith & Nephew of Memphis, Tenn., a Summit hip system available from Depuy J&J of Warsaw, Ind., and an Epoc Hip System available from Biomet of Warsaw, Ind.

The placement of the acetabulum component 10 in the acetabulum 121 is critical to the success of the hip replacement procedure. Therefore, the method of determining the position of the component 10, and preparation of the acetabulum 121 are key features. Further, the methods and devices disclosed herein provide for repeatability between different patients with different anatomical features.

The hip replacement procedure may access the femur 110 and acetabulum 121 through various surgical approaches, including: approaches posterior to the trochanter such as the Southern, Moore, Gibson, Kocher-Langenbeck, maximum splitting, and posterolateral approaches. Other approaches include those anterior to the trochanter such as Smith-Peterson, Rottinger, Heuter, direct anterior, Watson Jones, lateral, anterolateral, abductor split, trans-gluteal, Bauer, trans-lateral, and Hardinge. Additional approaches may include trans-trochianteric approaches. The methods and devices of the present application are applicable to procedures using any of these approaches, or any approaches that may be favored by particular surgeons.

Figure 3:
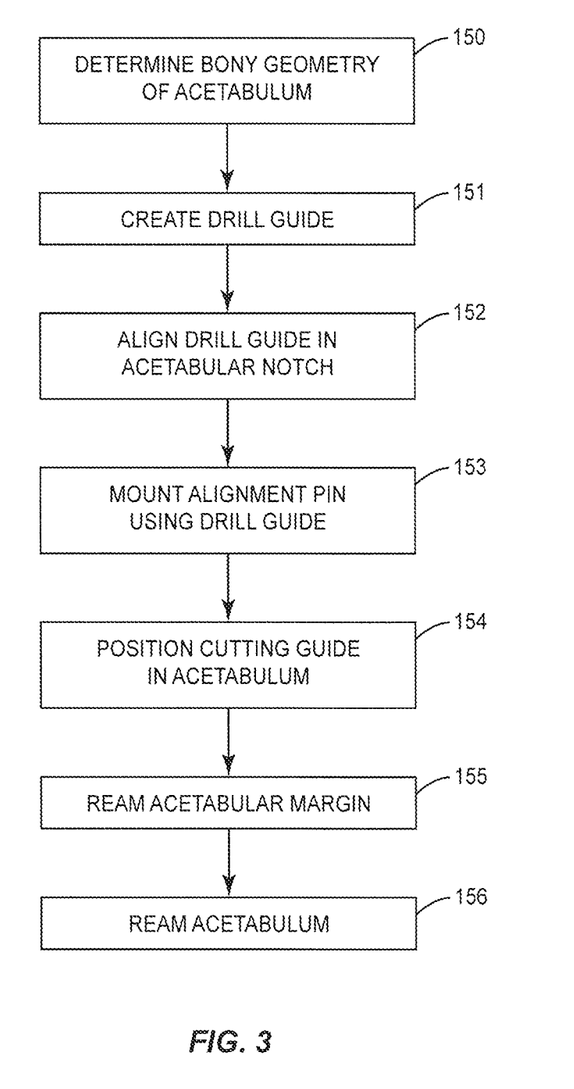
FIG. 3 is a flowchart diagram of the steps of preparing the acetabulum.

FIG. 3 illustrates the steps of preparing the acetabulum 121 for receiving an acetabular component 10. An initial step is to determine the bony geometry of the acetabulum 121 (step 150). The bony geometry may include but is not limited to the size, shape, and configuration of the acetabulum 121. This may occur through pre-operative and/or intra-operative planning. The bony geometry may be determined through various methods, including but not limited to computed tomography (CT) scans, magnetic resonance imaging (MRI) scans, X-ray imaging, and physical measurements of the acetabulum 121, such as intraoperative measurements obtained after accessing the acetabulum 121. This may also include data obtained through placement of templates of prosthetic silhouettes over the various images. The templates have multiple sizes matching the multiple sizes of the available implants. The templates provide a reasonably accurate prediction of the final components size and placement.

Figure 4:
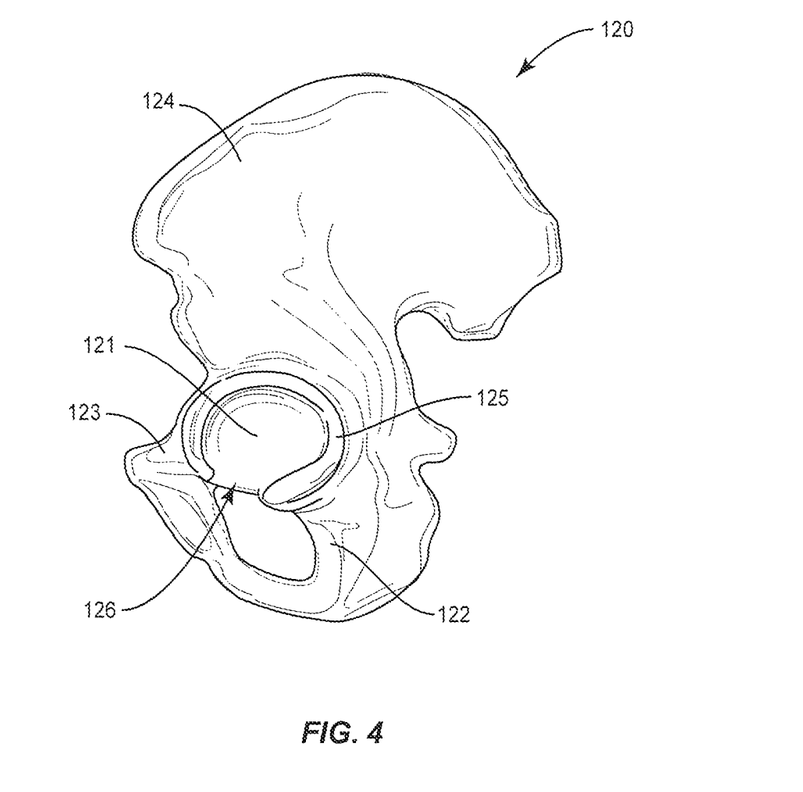
FIG. 4 is a left side view of the acetabulum and pelvis.

FIG. 4 illustrates a side view of the pelvis 120 and acetabulum 121. The acetabulum 121 is formed in part by the ischium 122, pubis 123, and ilium 124. The acetabulum 121 is a concave cavity and includes an acetabular margin 125 that extends around a majority of its rim. An acetabular notch 126, also referred to as a tear drop, is positioned along the acetabulum 121 and interrupts the margin 125. The notch 126 is continuous and converted into a foramen by the transverse acetabular ligament (not illustrated). The margins of the notch 126 serve for attachment of the ligamentum teres.

It has been determined that the notch 126 provides an accurate and consistent basis for establishing measurements and positioning of various guides and instrumentation for the preparation of the acetabulum 121. Further, it has been determined that the anatomy of other features of the acetabulum 121, such as the margin 125, have variations in their bony geometries between different patients. Therefore, measurements and positioning based on these other features result in a wide variation in positioning and measurements of the acetabulum 121 between different patients. However, the present methods and devices utilize the notch 126 because there is little to no variation between patients in the anatomy of the notch 126. Therefore, the notch 126 serves as the baseline feature for the various positioning and measurements steps that subsequently occur during the acetabulum preparation.

The method further includes creating a drill guide 20 (step 151). The guide 20 is preferably created specifically for the patient using the results of the bony geometry measurements. In one embodiment, the drill guide 20 is created through rapid prototyping using one or more of the CT, MRI, X-ray, and physical measurement information previously obtained of the acetabulum 121. In one embodiment, the guide 20 is created using 3D printing technology. In this manner, the guide 20 is created with the specific sizing and dimensions that conform to the specific patient bony geometry. The guide 20 may be created during pre-operative planning, or may be created during the surgical procedure (i.e., intra-operatively). One system for creating the guide 20 may include Solidscape 3D software available from Solidscape, Inc.

Figures 5A, 5B:
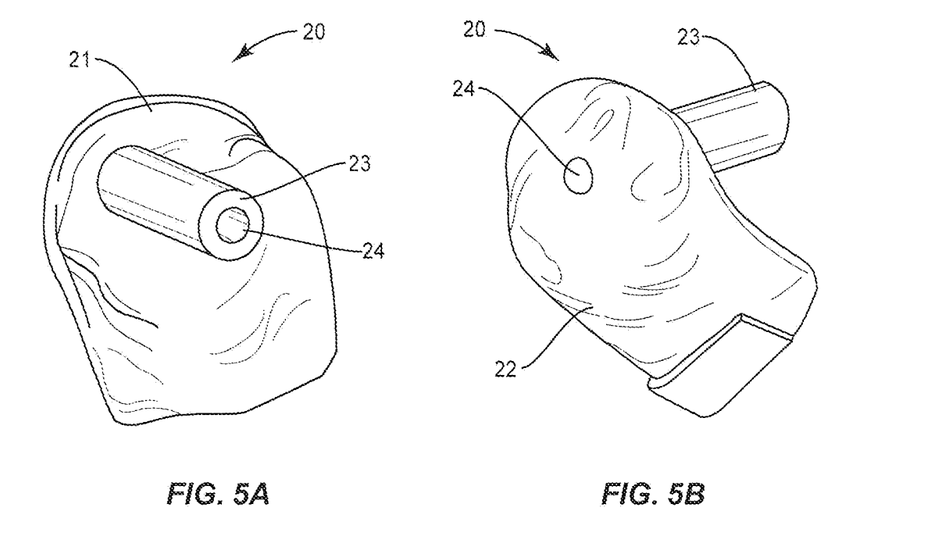
FIG. 5A is a perspective view of an inner side of a drill guide.
FIG. 5B is a perspective view of an outer side of a drill guide.

FIGS. 5A and 5B illustrate an embodiment of the drill guide 20 which includes a concave shape that matches the geometry of the acetabulum 121. The outer side 22 may include various configurations that mirror the bony geometry of the acetabulum 121. The inner side 21 may match the outer side 22, or may include a more uniform shape. A tube 23 extends outward from inner side 21. The tube 23 is hollow with an opening 24 that extends through the length. The opening 24 functions to guide a drill bit and alignment pin as will be explained in detail below.

Figure 6:
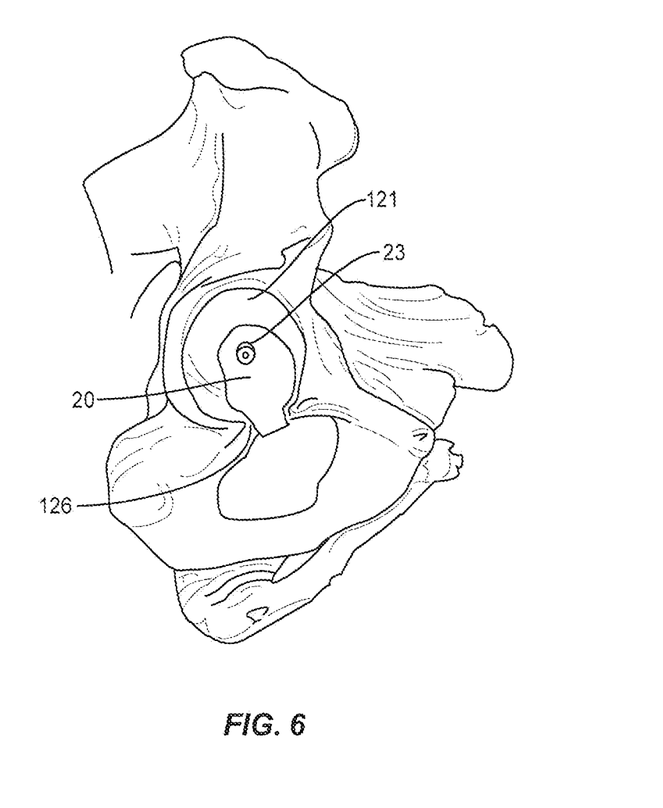
FIG. 6 is a side view a drill guide positioned within the acetabulum.

The drill guide 20 is sized and shaped to be mounted in the acetabulum 121 as illustrated in FIG. 6. The drill guide 20 is specifically sized and shaped to be positioned in the acetabular notch 126 (step 152). A portion of the outer side 22 mirrors the acetabular notch 126 such that the guide 20 can be precisely aligned within the acetabulum 121. The remainder of the guide 20 extends into the acetabulum 121 with the tube 23 aligned at a predetermined point at an interior of the acetabulum 121. In one embodiment, the tube 23 is aligned at the center point of the acetabulum 121.

The consistency of the acetabular notch 126 between different patients and the precise matching of the bony geometry of the acetabulum 121 provides for the guide 20 to precisely position the tube 23 at a predetermined point for each patient on which this method is used. Prior art methods have used other features of the acetabulum 121, such as the acetabular margin 125, for a baseline on which to prepare the acetabulum. However, there is a wide variation in the bony geometry of these features between different patients. Therefore, these methods result in different placements of the various guides and device between the different patients.

Figure 7:
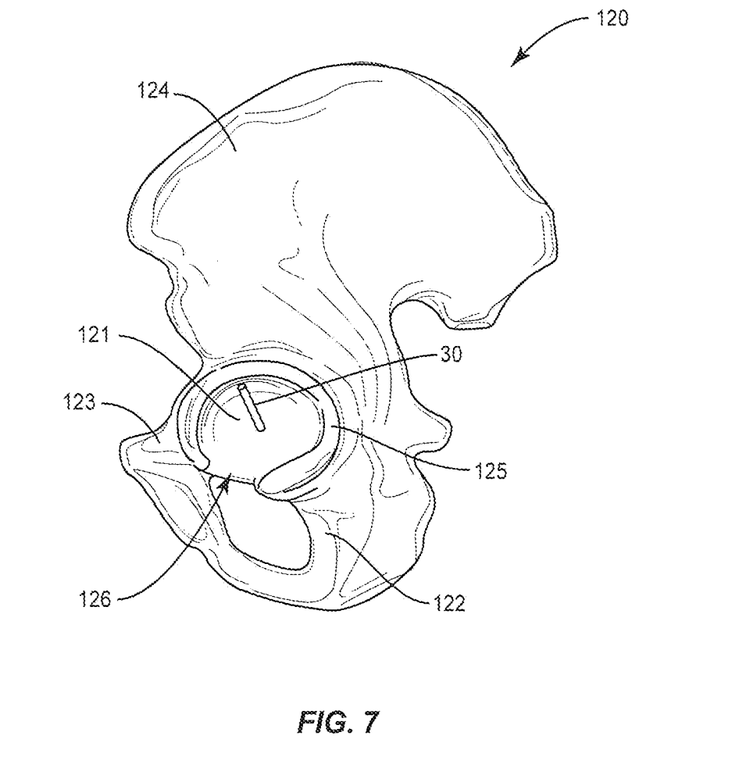
FIG. 7 is a left side view of an alignment pin positioned in the acetabulum.

An alignment pin 30 is then mounted in the acetabulum 121 (step 153). As illustrated in FIG. 7, the alignment pin 30 is a straight elongated member with a first end that mounts in the acetabulum 121 and an opposing second end that extends outward from the acetabulum 121.

Prior to mounting the pin, the surgeon may prepare a hole in the acetabulum 121 by inserting a drill bit through the opening 24 in the drill guide 20 and forming the hole at the predetermined point in the acetabulum 121. Once created, the alignment pin 30 is inserted and fixed in the hole. In one embodiment, the guide 20 is removed from the acetabulum 121 prior to mounting the pin 30 into the hole. Another embodiment includes the pin 30 being inserted through the opening 24 in the guide 20 and into the hole, followed by the guide 20 being lifted up along the pin 30 and away from the acetabulum 121.

Figure 8A:
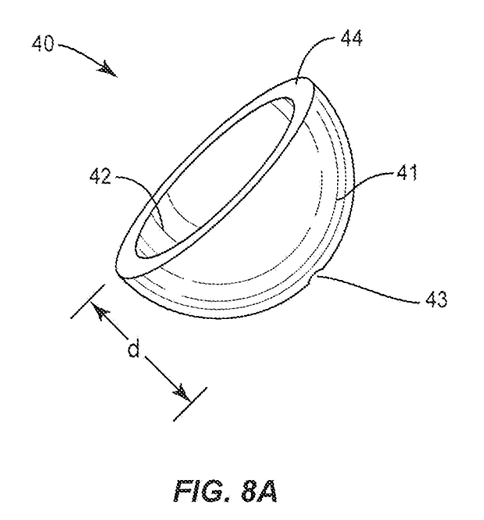
FIG. 8A is a perspective view of a cutting guide.
Figure 8B:
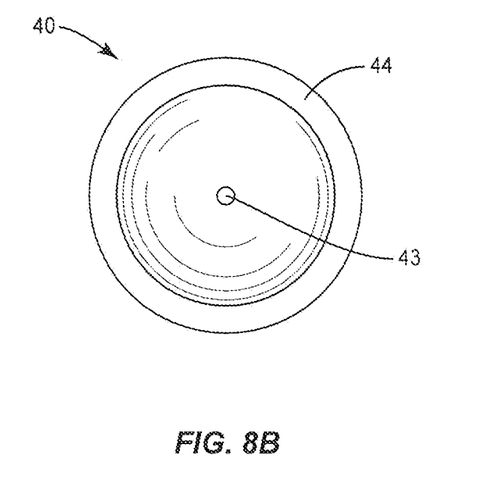
FIG. 8B is an end view of an open end of the cutting guide of FIG. 7A.

The pin 30 is then used to position a cutting guide 40 within the acetabulum 121 (step 154). FIGS. 8A and 8B illustrate a cutting guide 40 that includes a partial spherical shape with a closed first end and an open second end. The guide 40 includes a depth d measured between the closed first end and the open second end. In one embodiment, the guide 40 includes a hemispherical shape. In one embodiment, the guide 40 is roughly the same shape and size as the shell 11 (See FIG. 2). The outer side 41 is sized to generally conform to the shape of the acetabulum 121. The inner side 42 may mimic the outer side 41 causing a constant wall thickness throughout, or may include a different shape resulting in various wall thicknesses. A flat rim 44 extends between the outer and inner sides 41, 42.

An opening 43 is positioned at the closed bottom end and is sized to receive the alignment pin 30. The opening 43 may simply extend through the body, or may further extend through a tube (not illustrated) that extends upward from the inner side 42 (similar to the tube 23 of the guide 20). The tube includes a length such that the exposed outer end is recessed below the rim 44 to prevent interference with the reamer 50.

Figure 9:
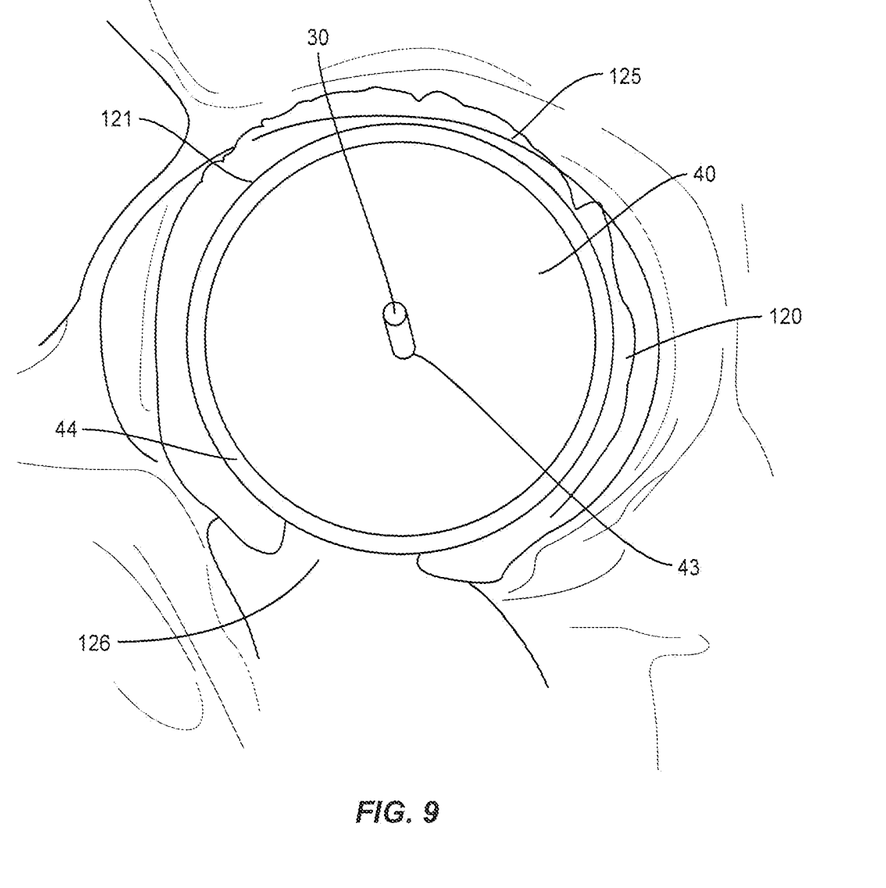
FIG. 9 is a perspective view of a cutting guide positioned in the acetabulum.

FIG. 9 illustrates the guide 40 positioned within the acetabulum 121. The guide 40 is positioned with the alignment pin 30 extending through the opening 43. The shape of the guide 40 allows it to seat within the acetabulum 121. The depth d of the guide 40 may be equal to or less than a depth of the acetabulum 121. This positions the rim 44 at or below the acetabular margin 125 that extends around a majority of the acetabulum 121. In one embodiment, the alignment pin 30 centers the guide 40 within the acetabulum 121.

Figure 10:
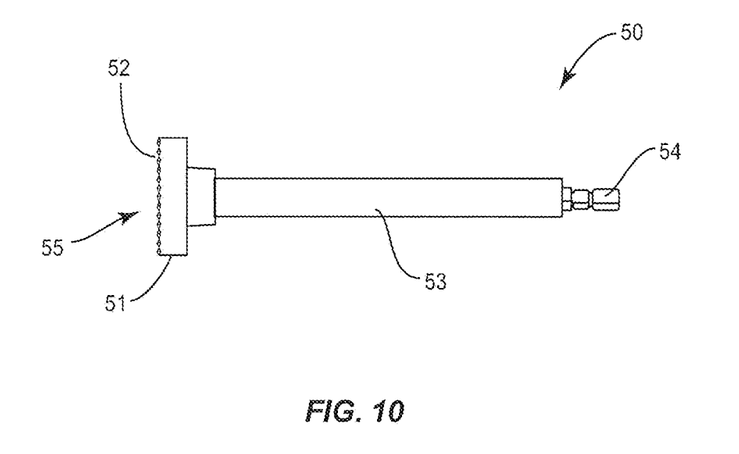
FIG. 10 is a side view of a reamer.

After placement of the guide 40, a reamer 50 is inserted over the alignment pin 30 to ream the acetabular margin 125 (step 155). FIG. 10 illustrates one embodiment of a reamer 50 that includes an enlarged head 51 with teeth 52 positioned at a distal end. The head 51 may include a circular shape when viewed axially. An elongated body 53 extends proximally from the head 51 and includes a mount 54 at a proximal end. The mount 54 is configured to engage with a powered device to rotate the reamer 50. Alternatively, the mount 54 is configured to receive a handle (not illustrated) for rotation by the surgeon. An opening 55 extends through the head 51 and at least along a distal portion of the body 53. The opening 55 is sized to receive the alignment pin 30.

In use, the opening 55 is positioned over the exposed proximal end of the alignment pin 30. The reamer 50 is moved along the pin 30 towards the acetabulum 121. The reamer 50 is rotated either by the powered device or by the surgeon prior to and/or after the teeth 52 are placed into contact with the acetabular margin 125. The movement along the pin 30 results in the reamer 50 having the proper approach angle relative to the acetabulum 121. Further, the rim 44 of the guide 40 acts as a depth stop to prevent over-reaming of the margin 125. The alignment pin 30 and the guide 40 provide for controlled movement of the reamer 50. This results in a uniform reaming of the margin 125. Further, the method is repeatable for different patients that each may include a different bony geometry. At the end of the reaming, each patient will have a reamed margin 125a that is then ready for further reaming of the interior concave surface of the acetabulum 121.

Figure 11:
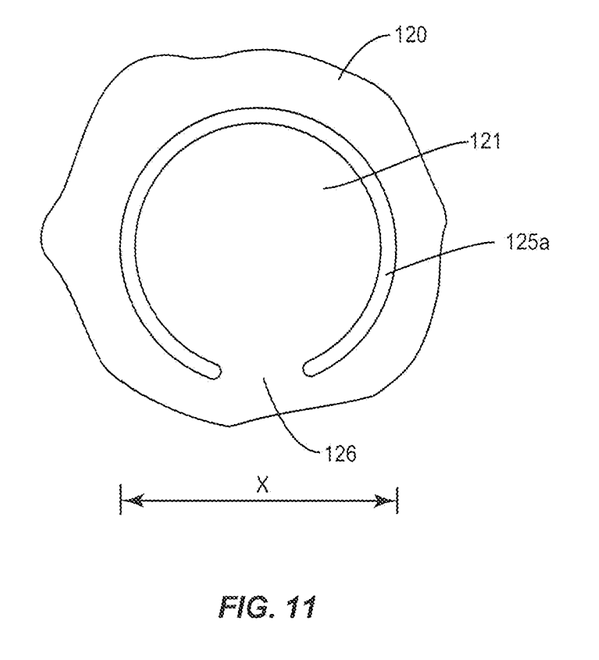
FIG. 11 is a schematic front view of a reamed acetabular margin that extends around a majority of the acetabulum 121.

Once the reaming is complete, the reamer 50, guide 40, and alignment pin 30 are each removed from the acetabulum 121. FIG. 11 schematically illustrates the reamed acetabular margin 125a. The reamer 50 forms an enlarged, substantially flat surface around the acetabulum 121. This surface controls the further reaming of the concave portion of the acetabulum 121.

Figure 12A:
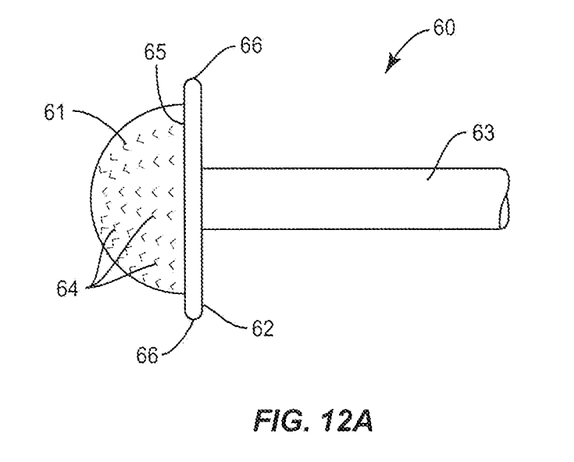
FIG. 12A is a side view of an acetabular reamer.
Figure 12B:
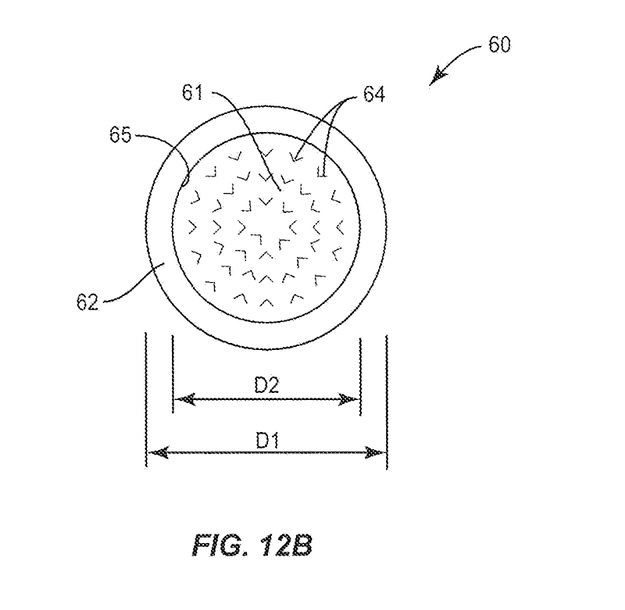
FIG. 12B is an end view of the acetabular reamer of FIG. 12A.

An acetabular reamer 60 is next used to ream the concave acetabulum 121 (step 156). The reamer 60 includes a head 61 with a concave shape. The shape and size of the head 61 may vary. Embodiments include the head 61 shaped and sized to match the shell 11 of the acetabular component 10. Teeth 64 are positioned about the head 61 to ream the acetabulum 121 as the reamer 60 is rotated and brought into contact. The size and location of the teeth 64 may vary depending upon the context of use. The body 63 extends proximally away from the head 61. The body 63 is configured to engage with a powered device to provide a rotational force to the reamer 60. Alternatively, the body 63 may be configured to receive a handle for the surgeon to manually apply a rotational force.

An enlarged flange 62 is positioned at a proximal end of the head 61. The flange 62 may extend completely around the perimeter of the head 61 as illustrated in FIGS. 12A and 12B, or may extend around limited sections of the head 61. In one embodiment, the flange 62 includes four equally-spaced sections that extend around a limited distance of the head with gaps formed between adjacent sections. The width D1 of the flange 62 is greater than a width D2 of the head 61. Further, the flange 62 includes an outer surface 65 that is substantially smooth. The outer surface 65 does not ream or otherwise cut the acetabulum 121 or reamed margin 125a upon contact. The flange 62 may further include a rounded outer perimeter 66. The flange 62 acts as a depth gauge and positioner while reaming the concave section of the acetabulum 121. The width D2 of the head 61 is less than a width X of the acetabulum 121, while the width D1 of the flange 62 is greater than the width X.

In use, the reamer 60 is moved into the patient with the head 61 contacting against the concave acetabulum 121 and the flange 62 riding above the margin 125a. The concave shape of the head 61 provides for simultaneously remaining multiple sections of the acetabulum 121. Further, the flange 62 acts as a depth stop by contacting against the margin 125a upon the full extent of reaming. The contact prevents the head 61 from reaming further into the concave section. Further, the flange 62 assists in controlling the proper approach angle of the reamer 60 into the acetabulum 121. In the event the approach angle is off, the flange 62 contacts the concave acetabulum 121. The smooth outer surface 65 and/or rounded outer perimeter 66 prevent reaming.

The reamer design further provides tactile feedback to the surgeon during the reaming process. The surgeon is able to feel the head 61 reaming the acetabulum 121 and the flange 62 riding along the margin 125a during reaming. The surgeon is also able to feel when the flange 62 contacts against the acetabulum 121 when the approach angle is incorrect.

Once reaming is complete, the surgeon removes the reamer 60. The acetabulum 121 is now ready to receive the acetabular component 10. The acetabular component 10 is placed within the patient and attached to the acetabulum 121 using various methods, including one or more bone screws. Bone screws may be used to attach the shell 11 to the acetabulum 121, with the liner 12 being subsequently placed over the bone screws and attached to the shell 11. The liner 12 is positioned to later receive the head 103 of the femoral component 101.

U.S. patent application Ser. No. 13/671,357 filed on Nov. 7, 2012 and titled "Methods and Devices for a Surgical Hip Replacement Procedure" and now published as U.S. Patent Publication No. 2014/0128987 discloses aspects of the hip replacement procedure and reaming of the femur 110 and acetabulum 121 and is herein incorporated by reference in its entirety.

In the embodiment disclosed above, the pin 30 is positioned in a central portion of the acetabulum 121. The pin 30 may also be positioned in other locations about the acetabulum 121 and the acetabular margin 125. In addition, multiple pins 30 may be positioned at various locations about the acetabulum 121 and/or acetabular margin 125. In one embodiment, multiple pins 30 are positioned along the acetabular margin 125.

The various methods and systems may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive.

What is claimed is:

1. A method of preparing an acetabulum for receiving an acetabular implant during a hip replacement procedure, the method comprising:
    aligning a first guide just in an acetabular notch of the acetabulum and determining a reference point in the acetabulum;
    removing the first guide from the acetabulum;
    after removing the first guide, positioning a second guide in the acetabulum and orienting the second guide with the reference point;
    while the second guide is positioned in the acetabulum, reaming an acetabular margin of the acetabulum with a reamer; and
    contacting the reamer against a rim of the second guide with the second guide preventing additional reaming of the acetabular margin below the rim of the second guide.

2. The method of claim 1, wherein aligning the first guide in the acetabular notch of the acetabulum and determining the reference point in the acetabulum comprises positioning a concave body of the first guide in the acetabulum and an extension that extends from the body in the acetabular notch.

3. The method of claim 1, wherein the second guide includes a partial spherical shape with a closed end that faces in towards the acetabulum and an open end that forms the rim and faces outward away from the acetabulum.

4. The method of claim 1, further comprising attaching an alignment member to the acetabulum at the reference point and positioning the second guide in the acetabulum while the alignment member is attached to the acetabulum.

5. The method of claim 4, further comprising reaming the acetabular margin while the alignment member is attached to the acetabulum.

6. The method of claim 1, further comprising positioning an opening of the first guide in the acetabulum and determining, the reference point in the acetabulum.

7. The method of claim 1, further comprising positioning a first portion of the first guide in the acetabulum and positioning a second portion of the first guide in the acetabular notch.

8. A method of preparing an acetabulum for receiving an acetabular implant during a hip replacement procedure, the method comprising:
    aligning a guide in the acetabulum by simultaneously positioning an extension of the guide just in an acetabular notch resulting in a body of the guide that is attached to and extends outward from the extension aligning in the acetabulum, the body of the guide including a concave shape that matches the acetabulum;
    determining an alignment point in the acetabulum using the guide;
    attaching an alignment member to the acetabulum at the alignment point;
    inserting a partially spherical cutting guide over the alignment member and aligning the cutting guide in the acetabulum with a flat rim at an open side of the cutting guide positioned at an acetabular margin of the acetabulum; and
    reaming the acetabular margin while the cutting guide is positioned in the acetabulum and controlling a depth of the reaming with the flat rim of the cutting guide.

9. The method of claim 8, wherein determining the alignment point in the acetabulum using the guide comprises aligning an opening in the guide with a center of the acetabulum by positioning the extension of the guide in the acetabular notch.

10. The method of claim 8, wherein attaching the alignment member to the acetabulum at the alignment point comprises inserting the alignment member through the body of the guide and attaching the alignment member to the acetabulum.

11. The method of claim 8, further comprising removing the guide from the acetabulum prior to attaching the alignment member to the acetabulum.

12. The method of claim 8, wherein reaming the acetabular margin comprises inserting a reamer over the alignment member and reaming the acetabular margin.

13. The method of claim 8, further comprising positioning a tube that extends outward from an inner side of the body of the guide at a center of the acetabulum.

14. A method of preparing an acetabulum for receiving an acetabular implant during a hip replacement procedure, the method comprising:
    aligning a guide relative to the acetabulum using just an acetabular notch by positioning a first portion of a guide just in the acetabular notch of the acetabulum and causing a second portion of the guide to be aligned in the acetabulum;
    using the second portion of the guide and determining a reference point in the acetabulum, the reference point being positioned within an acetabular margin;
    attaching an attachment member to the acetabulum at, the reference point with a free end of the attachment member extending outward from a surface of the acetabulum;
    attaching a cutting guide to the attachment member and aligning the cutting guide in the acetabulum with a flat rim at an open side of the cutting guide positioned at the acetabular margin of the acetabulum; and
    reaming the acetabular margin while the cutting guide is positioned in the acetabulum and controlling a depth of the reaming with the flat rim of the cutting guide.

15. The method of claim 14, further comprising removing the guide from the acetabulum prior to attaching the cutting guide with the attachment member.

16. The method of claim 14, wherein using the second portion of the guide and determining the reference point in the acetabulum comprises aligning an opening in the second portion of the guide with a center of the acetabulum.

17. The method of claim 14, further comprising reaming the acetabular margin while the attachment member is attached to the acetabulum.

* * * * *